United States Patent [19]

Carlier et al.

[11] Patent Number: 5,180,726
[45] Date of Patent: Jan. 19, 1993

[54] 4-[4- OR 6-(TRIFLUOROMETHYL-2-PYRIDINYL)]-1-PIPERAZINYL-ALKYL SUBSTITUTED LACTAMS

[75] Inventors: Patrick Carlier, Chatel-Guyon; Michel Combourieu, Cebazat; Claude Poisson, Riom; André J. Monteil, Chatel-Guyon, all of France

[73] Assignee: Akzo N.V., Arnhem, Netherlands

[21] Appl. No.: 777,963

[22] Filed: Oct. 17, 1991

[30] Foreign Application Priority Data

Oct. 23, 1990 [EP] European Pat. Off. ......... 90402980.8

[51] Int. Cl.$^5$ ................... A61K 31/495; C07D 401/14
[52] U.S. Cl. ..................................... 514/252; 544/364
[58] Field of Search .................... 544/364; 514/252

[56] References Cited

U.S. PATENT DOCUMENTS

| | | | |
|---|---|---|---|
| 3,907,801 | 9/1975 | Wu et al. | 514/252 |
| 4,242,343 | 12/1980 | Najer et al. | 544/374 |
| 4,543,355 | 9/1985 | Ishizumi et al. | 544/364 |
| 4,619,930 | 10/1986 | New et al. | 544/364 |
| 4,675,403 | 6/1987 | Abou-Gharbia et al. | 544/364 |
| 4,732,984 | 3/1988 | Abou-Gharbia | 544/364 |
| 4,977,167 | 12/1990 | Matsumura et al. | 514/326 |

FOREIGN PATENT DOCUMENTS 2114121  8/1983  United Kingdom ................. 544/364

OTHER PUBLICATIONS

Abou-Gharbia et al. J. Med. Chem. 31(7), 1382–1392 (1988).

Primary Examiner—Cecilia Tsang
Attorney, Agent, or Firm—William M. Blackstone

[57] ABSTRACT

The invention relates to neuroleptic/antidepressant 4-[4- or 6-(trifluoromethyl)-2-pyridinyl]-1-piperazinylalkyl substituted lactam derivatives having the general structure of formula I:

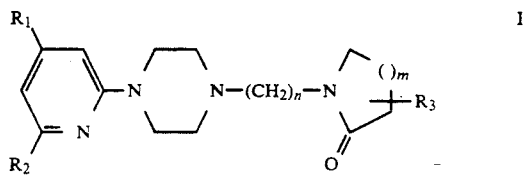

wherein one of the groups $R_1$ and $R_2$ is $CF_3$, and the other is hydrogen or $CF_3$;
  $R_3$ is hydrogen or (1–4 C) alkyl;
  n is an integer from 4 to 5; and
  m is an integer from 1 to 2; or pharmaceutically acceptable salts thereof.

The invention also includes processes for making the compounds and their salts.

6 Claims, No Drawings

4-[4- OR 6-(TRIFLUOROMETHYL-2-PYRIDINYL)]-1-PIPERAZINYLALKYL SUBSTITUTED LACTAMS

This invention relates to psychoactive drugs for use in treating depression and other nervous disorders.

Although their mechanisms of action have not been fully elucidated, several drugs are known to be useful in the treatment of depressive, neurotic, or psychotic disorders. Drugs for treating depression (i.e. anti-depressants) include the well-known "tricyclics", characterized, chemically, by various tricyclic ring structures. One of these mood-elevating drugs, opipramol, also has neuroleptic ("antipsychotic") activity.

U.K. Patent GB 1,332,194 discloses, in Example 22, an agent having a 4-[6-(trifluoromethyl-2-pyridinyl)]-1-piperazinylalkyl group. This compound which displays tranquilizing action, however, possesses a cyclic imide moiety instead of a lactam group. Moreover, it has been found that the compounds of the present invention in comparison with said prior art compounds have either better oral activity or are devoid of dopaminergic activity.

U.K. Patent Application GB 2,023,594 discloses related compounds having antidepressant and antianxiety activity. These compounds, however, have pyrrolidinonealkyl and piperidinone-alkyl groups, the alkyl moiety of which has 1–3 carbon atoms. It has now been found that these short chain compounds exhibit only marginal activity, and that therapeutically useful compounds have alkyl chains containing 4 or 5 carbon atoms.

5-Trifluoromethyl-2-pyridinyl imide derivatives, which are serotonin-1A ("5-HT$_{1A}$") receptor ligands with potential anxiolytic action, are also disclosed in AbouGharbia et al., "Polycyclic Aryl and Heteroarylpiperazinyl Imides as 5-HT$_{1A}$ Receptor Ligands and Potential Anxiolytic Agents: Synthesis and Structure-Activity Relationship Studies", J. Med. Chem., 31(7), 1382–1392 (1988) at page 1386 (compound 25), at page 1387 (compound 37), and at page 1388 (compounds 48 and 56). The reported serotonin (5-HT$_{1A}$) binding levels for these compounds (e.g. 72% for compound 48 at a 1 μmol concentration), however, were too low for practical pharmaceutical use. The invention relates to neuroleptic/antidepressant 4-[4- or 6-(trifluoromethyl)-2-pyridinyl]-1-piperazinylalkyl substituted lactam derivatives having the general structure of formula I:

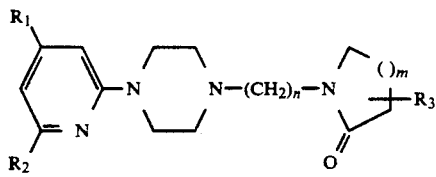

wherein one of the groups R$_1$ and R$_2$ is CF$_3$, and the other is hydrogen or CF$_3$;
R$_3$ is hydrogen or (1–4 C) alkyl;
n is an integer from 4 to 5; and
m is an integer from 1 to 2; or pharmaceutically acceptable salts thereof.

The invention also includes processes for making the compounds and their salts.

As more thoroughly described hereinafter, methods of making the compounds generally involve alkylating the terminal secondary amino portion of a 1-[4- or 6-(trifluoromethyl)-2-pyridinyl]piperazine derivative having formula II

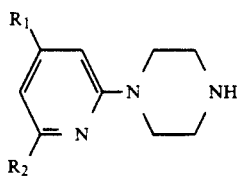

wherein R$_1$ and R$_2$ have the previously given meanings, with a lactam having formula III

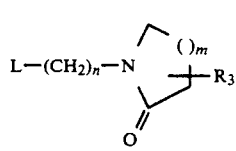

wherein R$_3$, n, and m have the previously given meanings, and L represents a leaving group. Suitable leaving groups are groups known as leaving group in alkylation reactions, such as halogens (especially chlorine, bromine, and iodine) or sulphonyl groups like the p-toluenesulphonyl and methanesulphonyl group.

Another method of preparation is the alkylation of the terminal secondary amino portion of the 1-[4- or 6-(tri-fluoromethyl)-2-pyridinyl]piperazine derivative having formula II, with a compound having the formula L-(CH$_2$)$_n$-OH, wherein L and n have the previously given meanings, after which the hydroxy group is converted into a leaving group, as previously defined. The resulting synthon is then condensed in alkaline medium with 2-pyrrolidinone or with 2-piperidinone (δ-valerolactam), which are optionally provided with a (1–4 C) alkyl group (i.e. methyl, ethyl, propyl, isopropyl, butyl, isobutyl, sec-butyl or tert-butyl). The novel compounds of formula I may be isolated from the reaction mixture in the form of a pharmaceutically acceptable salt. The pharmaceutically acceptable salts may also be obtained by treating the free base of formula I with an organic or inorganic acid such as HCl, HBr, HI, H$_2$SO$_4$, H$_3$PO$_4$, acetic acid, propionic acid, glycolic acid, maleic acid, malonic acid, methanesulphonic acid, fumaric acid, succinic acid, tartaric acid, citric acid, benzoic acid, or ascorbic acid.

When R$_3$ is alkyl, the compounds of this invention possess a chiral carbon atom, and may therefore be obtained as a pure enantiomer, or as a mixture of enantiomers, among which the racemic mixture. Methods for obtaining the pure enantiomers are well known in the art, e.g. synthesis with chiral induction, crystallization of salts which are obtained from optically active acids and the racemic mixture, or chromatography using chiral columns.

The compounds of the present invention may be used in the treatment of mammals, including human beings. The compounds are then used medically to care for, or deal with, an existing problem. They may also be used prophylacticly to prevent the occurrence or reoccurrence of the behaviour. For example, the compounds are administered to exhibit undesirable (e.g. neurotic, psychotic, or depressive) behaviour. A sufficient amount of compound is administered on a mg/kg body mass basis, for a sufficient amount of time to decrease the undesirable behaviour.

The invention also includes the use of the described compounds in the manufacture of a medicament for the treatment and/or prevention of the occurrence or reoccurrence of psychotic, neurotic, and depressive disorders, or any of them.

Preferred compositions display improved preferential binding activity to the 5-$HT_{1A}$ receptors over the 5-$HT_{1B}$ receptor. Preferably the $pK_i$ (binding constant) of the 5-$HT_{1A}$ receptors will exceed the number 7, and most preferably exceed 8. The $pK_i$ of the 5-$HT_{1B}$ receptor will therefore be less than the $pK_i$ of the 5-$HT_{1A}$ receptor for a particular compound.

The compounds of formula I, wherein n is 4 and $R_3$ is hydrogen or (1-4 C) alkyl, are preferred. The group $R_3$ can be attached to any carbon atom of the cyclic amide moiety with the exception of the carbonyl carbon atom, but preferred, however, are the sites juxtapositioned to the nitrogen atom or the carbonyl group. More preferred are the compounds of formula I having n is 4, $R_3$ is hydrogen or methyl, and one of the groups $R_1$ and $R_2$ is hydrogen. Most preferred is the compound having formula I, wherein $R_1$ is $CF_3$, $R_2$ and $R_3$ are hydrogen, n is 4, and m is 1.

Administration of the described compounds is useful in the prevention and treatment of psychotic, neurotic and depressive disorders. For example, pharmaceutical compositions containing sufficient dosages of the active ingredients, either separately or with other active compounds, may be used to treat psychotic behaviour, neuroses, anxiety, depression, combinations of these disorders, or any other disease state susceptible to treatment by the described compounds.

The dosage administered will generally be dependent upon the kind of disorder to be treated, the type of patient involved, his age, health, weight, kind of concurrent treatment, if any, length and frequency of treatment and therapeutic ratio of the particular compound.

The dosage forms will be administered over varying durations. To treat psychotic behaviour, neuroses, anxiety, depression, or combinations of these disorders, the compounds are administered to a patient for a length of time sufficient to alleviate the symptoms associated with the disorders that the patient is suffering from. This time will vary, but periods of time exceeding two weeks are especially preferred. After the symptoms have been alleviated, the compound may then be discontinued to determine whether it is still required by the particular patient. Some patients may require a lifetime of treatment.

Illustratively, dosage levels of the administered active ingredients can be between 0.1 mg and 10 mg per kg of body mass. In human therapy, daily doses of between 1 mg and 1000 mg, administered orally, will preferably be used. The pharmaceutical compositions containing the described compounds are preferably administered in unit dosage forms, such as tablets, capsules, pills, powders, granules, suppositories, sterile parenteral solutions or suspensions and non-parenteral solutions or suspensions, containing suitable quantities of an active ingredient or its pharmaceutically acceptable salt. For oral administration, either solid or fluid unit dosage forms can be prepared.

Methods and compositions for making such dosage forms are well-known to those skilled in the art. For example, methods and compositions for making tablets and pills containing active ingredients, methods of making powders and their composition, and methods for making solutions, emulsions, suspensions, or extractions for parenteral and intravenous administration are described in the standard reference, Chase et al., Remington's Pharmaceutical Sciences, (16th ed., Mack Publishing Co., Easton, Pa, U.S.A., 1980).

The term "unit dosage form" as used herein generally refers to physically discrete units suitable as unitary dosages for humans and animals, each containing a predetermined quantity of active material calculated to produce the desired psychotropic effect.

The invention is further illustrated by the following examples.

EXAMPLE I

Method of Making 1-(4-Bromobutyl)-2-Pyrrolidinone

To a suspension of 37 g of powdered KOH in 500 ml of tetrahydrofuran (THF) were added 25.2 g of tetraethylammonium bromide. Then, a solution of 51.6 g of 2-pyrrolidinone and 129.6 g of 1,4-dibromobutane in 100 ml of THF was added dropwise to the mixture. The mixture was heated and refluxed for 2 hours. The precipitate was filtered, and the THF evaporated. The residue was dissolved in dichloromethane, washed with water, and dried over anhydrous magnesium sulfate. The solvent was evaporated, and the residue distilled to yield 51.2 g of 1-(4-bromobutyl)-2-pyrrolidinone (38.8% yield) having a boiling point of 120° C. at 0.05 mm Hg.

B. Method of Making 1-[4-[4-[4-(Trifluoromethyl)-2-Pyridinyl]-1-Piperazinyl]Butyl]-2-Pyrrolidinone (E)-2-Butenedioate (1:1) Salt 2 7 g of 1-(4-bromobutyl)-2-pyrrolidinone were mixed with 2.2 g of 1-[4-(trifluoromethyl)-2-pyridinyl]-piperazine dissolved in 30 ml of butanol, after which 1.3 g of sodium carbonate were added. The mixture was refluxed for 2 hours, after which the precipitate was filtered and washed with butanol. The solvent was evaporated and the residue was dissolved in dichloromethane, washed with water, and dried over anhydrous magnesium sulfate. After evaporation of the solvent 3.4 g of 1-[4-[4-[4-(trifluoromethyl)-2-pyridinyl]-1-piperazinyl]butyl]-2-pyrrolidinone were obtained. To make the monofumarate, 1 g of fumaric acid dissolved in absolute ethanol was mixed with the free base. The resulting compound was recrystallized twice from acetonitrile, after which 2.4 g (52% yield) of 1-[4-[4-[4-(trifluoromethyl)-2-pyridinyl]-1-piperazinyl]butyl]-2pyrrolidinone (E)-2-butenedioate (1:1) salt were obtained with a melting point of 140° C.

EXAMPLE II

In a analogous manner as described in Example I was prepared:

1-[4-[4-[4-(trifluoromethyl)-2-pyridinyl]-1-piperazinyl]butyl]-2-piperidinone. M.p. 64° C.

1-[4-[4-[4-(trifluoromethyl)-2-pyridinyl]-1-piperazinyl]butyl]-3-methyl-2-pyrrolidinone (E)-2-butenedioate (1:1) salt. M.p. 152° C.

EXAMPLE III

Method of Making
1-[4-[4-[6-(Trifluoromethyl)-2-Pyridinyl]-1-Piperazinyl]Butyl]-2-Pyrrolidinone (E)-2-butenedioate (1:1) salt 9 g of 1-(4-bromobutyl)-2-pyrrolidinone and 7.6 g of 1-[6-(trifluoromethyl)-2-pyridinyl]-piperazine were mixed with 100 ml of butanol. 4.3 g of sodium carbonate were added, and the mixture is refluxed for 3 hours. The precipitate is filtered and washed with butanol, and the filtrate is then evaporated. The residue was dissolved in dichloromethane, washed with water, dried over anhydrous magnesium sulfate, after which the solvent was evaporated to obtain 12.5 g of 1-[4-[4-[6-(trifluoromethyl)-2-pyridinyl]-1-piperazinyl]-butyl]-2-pyrrolidinone. To make the monofumarate, the free base was mixed with 3.9 g of fumaric acid in absolute ethanol. The resulting substance was recrystallized twice from absolute ethanol, after which 7.8 g (43.6% yield) of 1-[4-[4-[6-(trifluoromethyl)-2-pyridinyl]-1-piperazinyl]-butyl]-2pyrrolidinone. (E)-2-butenedioate (1:1) salt were obtained. M.p. 173° C.

EXAMPLE IV

In a analogous manner as described in Example III were prepared:

1-[4-[4-[6-(trifluoromethyl)-2-pyridinyl]-1-piperazinyl]butyl]-2-piperidinone (E)-2-butenedioate (2:3) salt. M.p. 154° C.

1-[4-[4-[6-(trifluoromethyl)-2-pyridinyl]-1-piperazinyl]butyl]-5-methyl-2-pyrrolidinone (E)-2-butenedioate (1:1) salt. M.p. 137 C.

1-[4-[4-[6-(trifluoromethyl)-2-pyridinyl]-1-piperazinyl]butyl]-3-methyl-2-pyrrolidinone (E)-2-butenedioate (1:1) salt. M.p. 125° C.

We claim:

1. A 4-[4- or 6-trifluoromethyl)-2-pyridinyl]-1-piperazinylalkyl substituted lactam derivative having the structure:

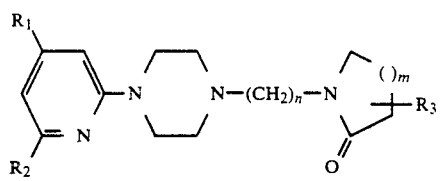

wherein one of the groups $R_1$ and $R_2$ is $CF_3$ and the other is hydrogen or $CF_3$;

$R_3$ is hydrogen or (1–4 C) alkyl;

n is an integer from 4 to 5; and m is an integer from 1 to 2; or a pharmaceutically acceptable salt thereof.

2. The compound of claim 1, wherein n is 4, and $R_3$ is hydrogen or (1–4 C) alkyl, or a pharmaceutically acceptable salt thereof.

3. The compound of claim 1 wherein n is 4, $R_3$ is hydrogen or methyl, and one of the groups $R_1$ and $R_2$ is hydrogen, or a pharmaceutically acceptable salt thereof.

4. The compound of claim 1 wherein $R_1$ is $CF_3$, $R_2$ and $R_3$ are hydrogen, n is 4, and m is 1, or a pharmaceutically acceptable salt thereof.

5. A method for preventing neurotic, depressive, or psychotic behaviour in a mammal comprising administering to said mammal a sufficient amount of the compound of claim 1, to prevent the occurrence of said neurotic, depressive, or psychotic behaviour in said mammal.

6. A pharmaceutical composition comprising an effective amount of the compound of claim 1 for treating a psychotic, neurotic or depressive disorder and a pharmaceutically acceptable carrier.

* * * * *